United States Patent [19]

Shields

[11] Patent Number: 5,061,250
[45] Date of Patent: Oct. 29, 1991

[54] INTRAVENOUS NEEDLE SHEATHING DEVICE

[76] Inventor: Jack W. Shields, 1950 Las Tunas Rd., Santa Barbara, Calif. 93103

[21] Appl. No.: 574,293

[22] Filed: Aug. 28, 1990

[51] Int. Cl.$^5$ .............................................. A61M 5/32
[52] U.S. Cl. ..................................... 604/198; 604/263
[58] Field of Search ................ 604/192, 198, 263, 163

[56] References Cited

U.S. PATENT DOCUMENTS

| | | | | |
|---|---|---|---|---|
| 2,847,995 | 8/1958 | Adams | | 604/198 |
| 4,723,942 | 2/1988 | Scott | | 604/164 |
| 4,932,946 | 6/1990 | Shields | | 604/198 |

*Primary Examiner*—C. Fred Rosenbaum
*Assistant Examiner*—Corrine Maglione
*Attorney, Agent, or Firm*—Michael G. Petit

[57] ABSTRACT

A sliding slit elastomeric needle sheath is described for preventing needle-stick injuries from hollow-bore steel needles attached to trailing tubular assemblies used for giving intravenous infusions or withdrawing blood. The sheath comprises a slit elastomeric tube with a leading end and a trailing end, the trailing end of which slides over the silastic tubing in standard butterfly and phlebotomy assemblies, or onto the leading end of vacutainer needle hubs, until the trailing end of the sheath locks with compression onto the hub of the needle used for venepuncture. The mid-portion of the sheath is surrounded by a securely attached puncture-resistant scabbard. The slit elastic tube is stretched by manual traction to enclose or expose the venepuncture needle. The leading end of the sheath includes a flexible tender with a tab for guiding the sharp needle tips safely and accurately through combinations of rigid and slit elastic parts to prevent needle-stick injuries during and after withdrawal of the needle from the vein of a patient by a user whose hands operate in customary positions.

6 Claims, 2 Drawing Sheets

INTRAVENOUS NEEDLE SHEATHING DEVICE

BACKGROUND OF THE INVENTION

1. Field of the Invention.

Needle-stick injuries from hollow-bore steel needles used for withdrawing venous blood or giving intravenous infusions have become the most common cause of AIDS and serum hepatitis in health care personnel exposed to infected individuals at work. Currently, there are urgent needs for reliable, effective and inexpensive ways to prevent such injuries.

This invention relates to sliding protective needle sheaths for use with intravenous infusion, phlebotomy sets, or the like.

2. Description of the Prior Art

The use of disposable puncture-resistant scabbards attached by friction to needle hubs for protecting hollow-bore steel needles before and after use has been standard practice for more than 30 years. However, the threat of AIDS and serum hepatitis from needle-stick injuries during the manual resheathing of needles with such scabbards after intravenous, intramuscular or subcutaneous use has made it imperative to find safer ways to protect the sharp needle tips.

Open-ended puncture-resistant needle protectors which slide forward with manual manipulation over trailing assemblies to lock with the open ends just beyond the tips of hollow-bore steel needles are known in the art. Factors limiting general use are:

a. The costs of production.

b. They are difficult to manipulate without considerable practice and dexterity, especially if the user employs one hand to maintain pressure over a venepuncture site and single-handedly attempts to securely lock a sliding needle protector over the hazardous tip of a withdrawn needle.

The concept of inserting such scabbards into slit elastomeric tubes, or inserting such slit elastomeric tubes into the scabbards, such that the scabbards are secured by elastic forces is described in U.S. Pat. No. 4,932,946. It is useful to adapt the slit elastomeric sheathing system taught in U.S. Pat. No. 4,932,946 to intravenous infusion and phlebotomy sets wherein a tube is attached to the trailing end of the venepuncture needle.

SUMMARY OF THE INVENTION

Sliding slit elastomeric tubes as are known in the prior art are adapted to be used for safely housing intravenous needles immediately after use with assemblies intended for withdrawing blood or giving intravenous infusions. The prior art tubular needle sheaths have a leading end, a mid-portion and a trailing end. The trailing end is adapted to slide over silastic tubing, thereby permitting location of the entire sheathing system away from the needle until needed.

Outstanding features of such improved elastomeric intravenous needle sheaths are:

1. They can be made inexpensively because they require no locking or specially fabricated moving parts other than short segments of elastomeric tubing, such as silicone tubes which can be made very elastic and can be slit easily, but maintain great tensile strength to prevent splitting or splaying beyond the leading and trailing ends of the slits.

2. They can be applied during fabrication to existing winged infusion or phlebotomy sets without causing significant changes in manufacturing procedures, other than slipping the improved sheaths over the silastic tubing before the trailing hubs are attached.

3. The adapted sheaths can be temporarily attached to the trailing hubs at points distant from the leading needle hubs, allowing the users to insert the needles into veins without encumbrance.

4. They can be made easy to use with hands in normal use positions during withdrawal of hollow-bore steel needles from veins.

6. In the case of phlebotomy sets with sharp hollow-bore steel needles on each end, each end could be handled similarly to protect the tips of both needles.

7. Properly used, there is very little lag time after the user withdraws the needle from the vein of a patient until the hollow-bore needle is safely covered. Subsequently, the needle, proximal tubing or double-tipped vacutainer needle can be transported sooner or later to the nearest safe container with minimal chance of straight on or tangential needle-stick injury to the user, to anyone located nearby or to health workers concerned with cleaning up after usage.

DESCRIPTION OF THE PREFERRED EMBODIMENTS

A. First Preferred Embodiment

Figure 1:
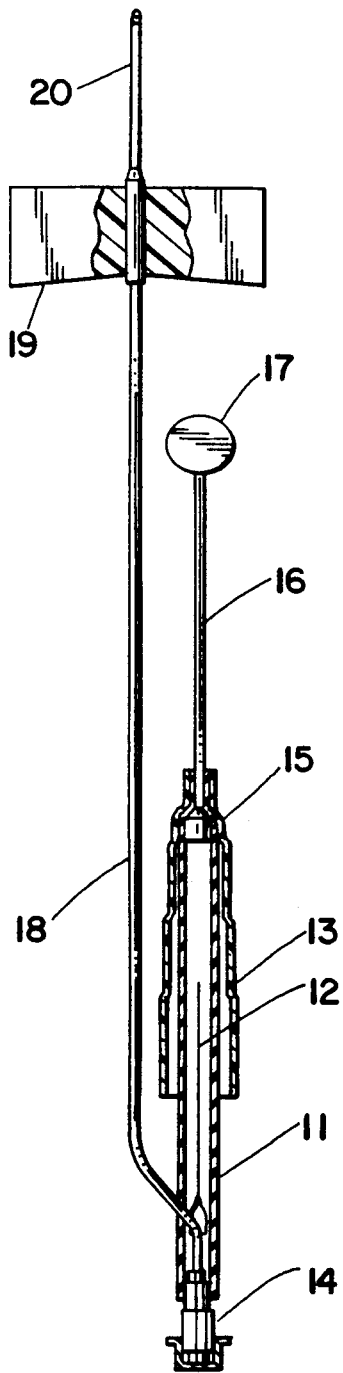
FIG. 1 a cutaway schematic view of the sliding slit elastomeric needle sheath of the present invention attached to the trailing hub of a winged infusion set.

The sliding slit elastomeric needle sheath comprising the first preferred embodiment of the present invention can be understood by looking first at FIG. 1. The sheath (11) consists of a single section of elastomer tubing having a longitudinal slit (12) in its mid-portion. The sheath's leading end (15) is securely attached to a puncture-resistant rigid plastic scabbard (13) and to a flexible, but non-stretchable tether (16), preferably by compression locking of the elastic sheath inside the scabbard and chemical or physical bonding of the trailing end of the tether to the leading end of the scabbard. The trailing end of the elastomeric tubular sheath is initially attached loosely by sliding and stretching onto the trailing hub (14) of a winged infusion set whose leading "butterfly" needle hub (19) and trailing infusion hub are connected by intervening tubing (18) which passes through the slit (12) in the elastomeric tube on its course to the trailing hub of a hollow-bore steel needle (20) used for drawing blood or giving intravenous infusions. Thus, the slit in the elastomeric tubing serves as a means of sliding the needle sheath over intervening silastic tubing (18), as well as an opening to enclose the needle (20). Before use, the needle (20) is usually protected by a disposable tubular scabbard (not shown), held by friction to the leading portion of the needle hub. This scabbard helps keep the needle sterile until use, and is always discarded, because it is now considered too hazardous to put back on after the needle has been inserted into a vein.

Figure 2:
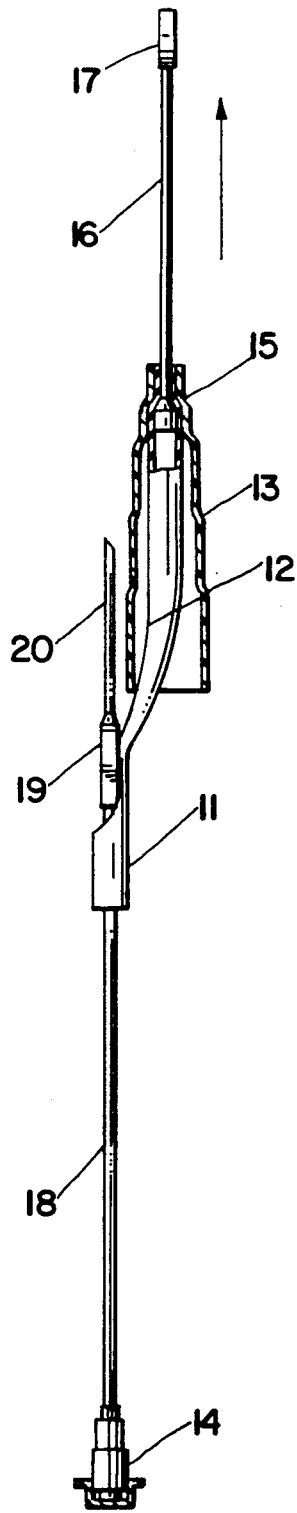
FIG. 2 a schematic representation of the sheath of FIG. 1 with the sheath slid forward to grasp the trailing end of a winged infusion needle hub.

As shown in FIG. 2, after the needle (20) has been used, finger traction in the direction of the arrow on the tab (17) portion of the tether (16), together with loosening of the temporary attachment of the elastomeric tubular sheath (11) to the trailing hub (14), will enable the sheath to slide forward over the silastic tubing (18) until its slit (12) becomes splayed and unable to pass over the trailing portion of the needle hub (19). At this point, the leading part of the slit (12) and the puncture-resistant scabbard will overlie the hollow-bore steel needle whose tip is still submerged under the patient's skin.

Figure 3:
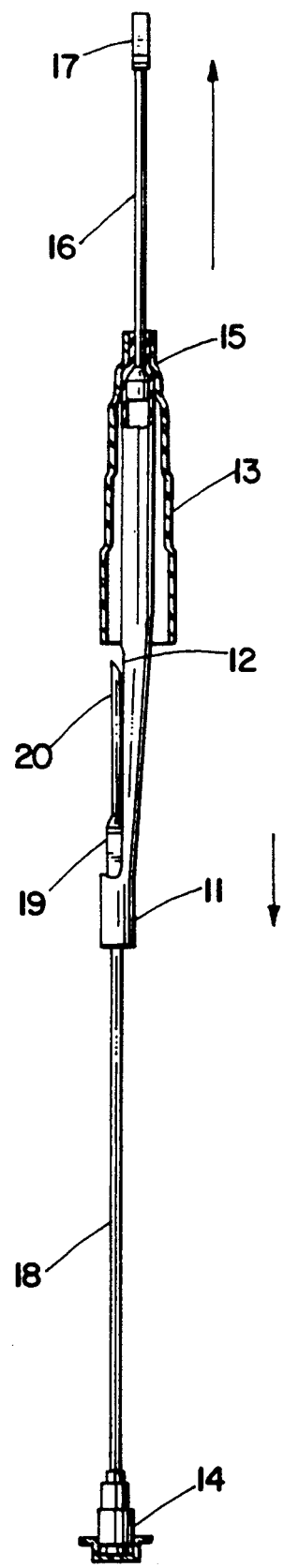
FIG. 3 a schematic view of the sheath of FIG. 2 with the slit elastomeric tube stretched enough to enclose the hollow-bore steel needle.

As shown in FIG. 3, further traction on the tether tab (17) will stretch the elastomeric tube (11) and the slit (12) contained therein until the puncture-resistant scabbard (13) lies beyond the sharp tip of the needle (20), provided that the needle hub (19) is stabilized or pulled backward in the direction of the arrow at (19).

Figures 4, 5, 6:
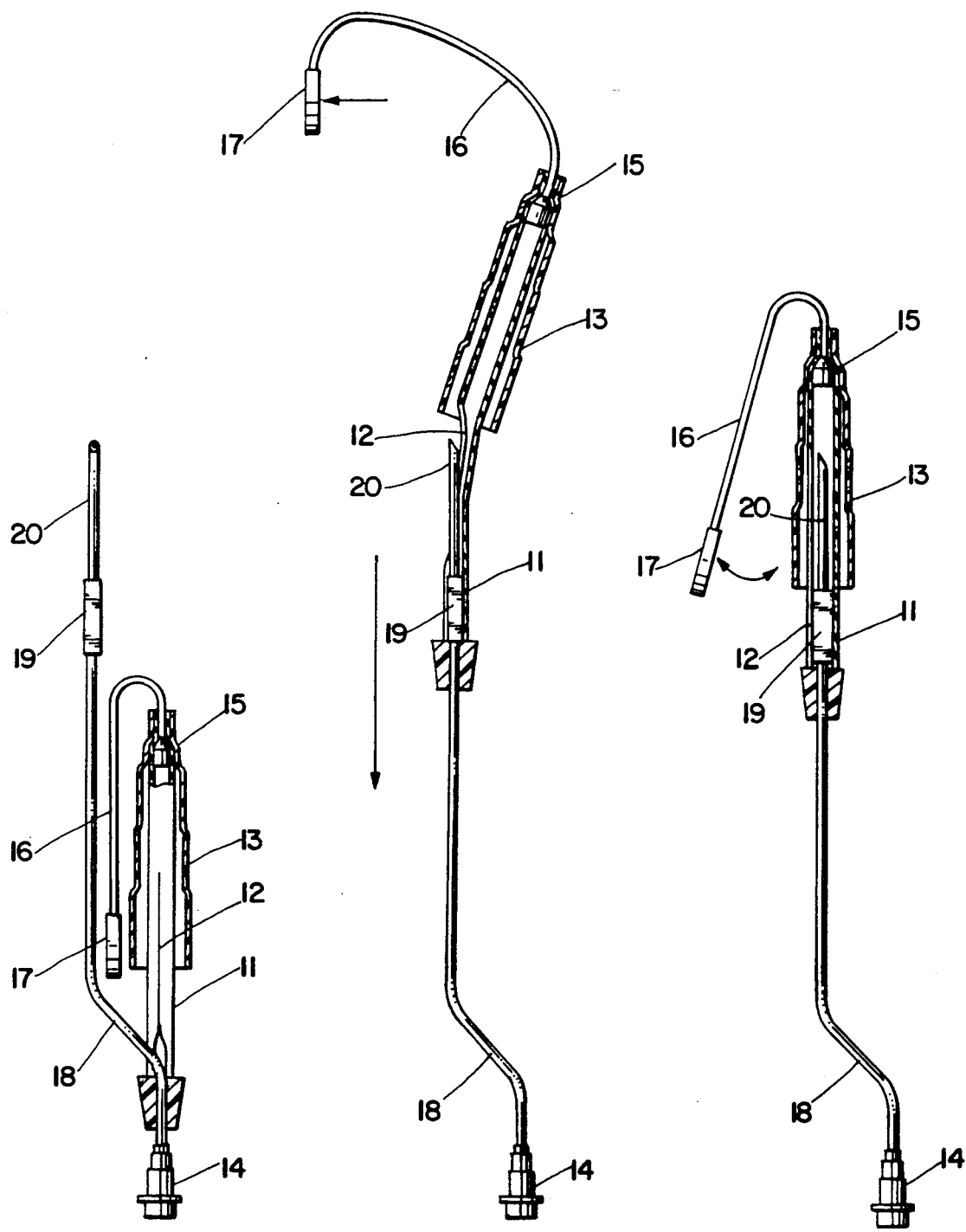
FIG. 4 a schematic view of the sliding slit elastomeric needle sheath of FIG. 1, with both the needle and sheath.
FIG. 5 a schematic representation immediately preceding resheathing of the needle with the tether tab pressed against the puncture site to stem the bleeding.
FIG. 6 a schematic view of the sheath of FIG. 5 with the tether released and the slit elastomeric tube enclosing the hollow-bore steel needle.

As shown in FIG. 4, in order to conserve space in packaging, the tether is folded out of the way and doubled back alongside the puncture-resistant scabbard (13) before use.

As shown in FIG. 5, effective use commences when the protective assembly is displaced forward over the silastic tubing (18) and the user places the tab (17) over the venepuncture site. Firm application of downward pressure on the tab in the direction of the arrow prevents venous bleeding and supplies a firm base for use of the tether (16).

Finally, as shown in FIG. 6, continued downward pressure on the tab (17), coupled with backward manual traction on the needle hub (19) will remove the needle (20) from a patient's vein and, simultaneously, pull on the tether (16) until it becomes taut enough to stretch the hub-anchored elastomeric tubing (11) and slit to the point that the needle will be captured inside elastomeric tubing and the surrounding puncture-resistant scabbard (13). Relaxation of traction, then, will leave the hollow-bore steel needle safely enclosed, as schematically shown in FIG. 5. Subsequently, the entire assembly consisting of the protected needle, the elastic sheathing system, and all trailing parts can be safely disposed immediately or later with minimal risk of needle-stick injury.

It should be added that the tether (16) must be made of flexible, but inelastic material of suitable length so that a solid system is sustained for manual traction between the tab (17) and the needle hub (19) and so that there is plenty of room between the finger holding down the tab and the needle when it emerges form the patient's skin. Moreover, the tether must be inelastic, so that the needle will not be pulled toward the tab in the event that the user inadvertently lets go of the trailing assembly.

The proper procedure for removing and resheathing the needle is as follows for a right handed user:

a. He/she would use the left hand to slide the assembly forward until the trailing end of the slit elastomeric sheath grasps the trailing end of the needle-containing hub of a winged infusion or phlebotomy set after use for intended purposes.

b. He/she would place the tab on the tether directly over a venepuncture site previously covered by a sterile cotton pledget.

c. With the left thumb or forefinger applying pressure over the venepuncture site to control bleeding, as well as anchor the leading end of the tether, he/she would grasp the winged or large diameter leading hub of the infusion set to pull the hollow-bore steel needle straight back.

d. He/she would continue gentle traction until the slit in the stretched elastomeric tube captures the entire needle.

e. He/she would then release the traction supplied by firm anchorage of the tether tab and pulling back on the leading needle hub, thus leaving the hollow-bore steel needle safely enclosed within the elastomeric tube, in turn surrounded by a rigid puncture-resistant scabbard.

f. He/she would continue to hold left-handed pressure on the tether tab and underlying sterile cotton pledget until the patient's venous bleeding was effectively stopped; while the relaxed right hand would hold the hub of a safely enclosed hollow-bore steel needle.

g. Alternatively, he/she would temporarily release pressure over the venepuncture site long enough to free the tether tab, but resume left-handed pressure; while the right hand sooner or later disposes of the safely covered hollow-bore steel needle and the proximal apparatus to which the needle is attached. (This alternative would probably constitute a preferred usage in the case of use with vacutainer assemblies).

B. Second Preferred Embodiment

The second preferred embodiment is similar to the first, except that the sliding slit elastomeric sheath with scabbard is applied to phlebotomy assemblies with leading and trailing hubs of differing configurations. In the case of phlebotomy assemblies with a single needle-containing hub, the hub must be of sufficiently large diameter to prevent forward sliding of the protective elastomeric assembly in the usage position, or be fitted with protuberances which will not allow the trailing end of the slit elastomeric tubes to slide forward beyond the use position. In the case of phlebotomy assemblies with needle-containing hubs at each end, a protective assembly should be provided for both ends.

C. Third Preferred Embodiment

A third preferred embodiment can be fabricated wherein the slits in the trailing ends of the elastomeric tubes are extended to the very ends, and partially surrounded there by open, but rigid collars, (21) of FIGS. 4–6, which allow the slits to slide over or onto the trailing ends of leading hubs of winged infusion sets, phlebotomy sets or vacutainer needles. Securely attached there by compression, before the hollow-bore steel needle is withdrawn from a vein, the user would then proceed to protect this needle as outlined in the First Preferred Embodiment. This third preferred embodiment has the advantage that the improved elastomeric needle sheaths can be attached by the user to infusion, phlebotomy or vacutainer assemblies currently available. However, this third embodiment would be more expensive to produce.

The foregoing embodiments are provided to instruct in the use of the invention. The scope of the invention is not limited to the particular embodiments described herein.

What I claim is:

1. An intravenous needle sheath for preventing accidental needle-stick injuries, said needle sheath being adapted for use with an intravenous infusion or phlebotomy set, said intravenous infusion or phlebotomy set comprising a length of tubing of substantially uniform diameter, said tubing having a leading end permanently affixed to the hub of an intravenous hollow bore steel needle and a trailing end; said intravenous needle sheath comprising:
   (a) an elastomeric tube having leading and trailing ends and a mid-portion therebetween and an outer wall and inner lumen with at least one axially oriented slit in its outer wall extending into the inner lumen,
   (b) a puncture-resistant scabbard securely affixed to the leading end of said elastomeric tube;
   (c) a flexible tether permanently affixed to the leading end of said elastomeric tube for grasping said elastomeric tube to apply manual traction to stretch said elastomeric tube; and
   (d) means on the trailing end of said elastomeric tube for slidably attaching said intravenous needle sheath to the leading end of said intravenous tubing permanently affixed to the trailing end of the hub holding said intravenous hollow bore steel needle.

2. The intravenous needle sheath of claim 1 wherein the inner lumen diameter of said elastomeric tube is greater than the outer diameter of said intravenous tubing, but smaller in diameter than the hub of said hollow bore steel needle.

3. The intravenous needle sheath of claim 2 wherein said axial slit in the mid-portion of said elastomeric tube does not extend to the trailing end.

4. The intravenous needle sheath of claim 1 wherein said axial slit extends the trailing end of said elastomeric tube and is reinforced by a collar which permits the trailing end of said intravenous needle sheath to slide over said intravenous tubing.

5. The intravenous needle sheath of claim 1 wherein said means on the trailing end of said elastomeric tube for slidably attaching said intravenous needle sheath to said intravenous tubing comprises a substantially circular collar affixed to the trailing end of said elastomeric tube, wherein the inside diameter of the collar is greater than the exterior diameter of said intravenous tubing.

6. The intravenous needle sheath of claim 1 wherein said puncture-resistant scabbard comprises a rigid, substantially cylindrical or conical puncture-resistant enclosure.

* * * * *